United States Patent [19]

Wechsler et al.

[11] 4,189,593

[45] Feb. 19, 1980

[54] PROCESS FOR MAKING IMIDAZOLINES

[76] Inventors: Joseph R. Wechsler, 7621 Sheridan, Chicago, Ill. 60626; Thomas G. Baker, 3500 Forest, Wilmette, Ill. 60091; George T. Battaglini, 582 White Pine Rd., Buffalo Grove, Ill. 60090; Frank L. Skradski, 161 Park Ave., Grayslake, Ill. 60030

[21] Appl. No.: 901,712

[22] Filed: May 1, 1978

[51] Int. Cl.² ............................................. C07D 233/16
[52] U.S. Cl. ..................................... 548/352; 252/8.8; 252/357
[58] Field of Search ........................................ 548/352

[56] References Cited

U.S. PATENT DOCUMENTS

| | | | |
|---|---|---|---|
| 2,267,965 | 12/1941 | Wilson | 548/352 |
| 2,484,146 | 10/1949 | Barker et al. | 548/352 |
| 3,408,361 | 10/1968 | Mannheimer | 548/352 |
| 4,121,009 | 10/1978 | Chakrabarti | 428/260 |

OTHER PUBLICATIONS

Chem. Abst. 1964, vol. 60, p. 13251e.

*Primary Examiner*—Alan L. Rotman
*Assistant Examiner*—Natalia Harkaway
*Attorney, Agent, or Firm*—Hill, Van Santen, Steadman, Chiara & Simpson

[57] ABSTRACT

A process for making substituted imidazoline substantially completely free from diamide and preferably from byproduct ester. The process involves contacting an aminoethyl lower alkanol amine with a methyl carboxylate at elevated temperature and thereafter subjecting the reaction product to two successive heat treatments under specified conditions. A feature of the process is that it contains an optional step which can be employed to correct the formation of unwanted amounts of ester in the product. The product imidazoline is useful as a starting material for making amphoteric surfactants.

17 Claims, No Drawings

PROCESS FOR MAKING IMIDAZOLINES

RELATED APPLICATION

The product produced by the process of the present invention may be used as a starting material for a further process discovered by applicants which further process has been made the subject matter of a copending U.S. application for patent filed on even date herewith and identified by U.S. Ser. No. 901,713.

BACKGROUND OF THE INVENTION

The prior art appreciates that substituted imidazolines can be prepared by reacting aminoethyl ethanol amine with carboxylic acids. Because fatty acids are not particularly selective in their reaction with aminoethyl ethanol amine between the primary and secondary amine functions, the fatty acid can react with the aminoethyl ethanol amine with either the primary amine or the secondary amine. As a consequence, appreciable amounts of diamide result as a side reaction product. The diamide so produced and the equation illustrating the reaction are theoretically as follows:

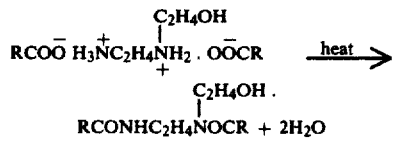

where R is as herein below defined.

The diamide by-product is undesirable because the diamide is inert, insoluble in water, and precipitates thereby causing objectionable turbidity in a final product produced by opening a substituted imidazoline ring in the presence of sodium chloroacetate.

In addition to the unwanted diamide, the indicated prior art process for making substituted imidazolines apparently also has inherently associated with it a tendency to produce a byproduct ester having a characteristic detectable infrared peak at 5.75 microns. The exact reaction causing the production of this ester is not certain, and the structure of this ester is likewise not certain, but it is theorized that this ester may have the structure:

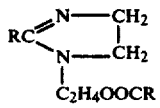

where R is as herein below defined. We wish to point out that we do not wish to be bound herein by theory.

The presence of such an ester in a substituted imidazoline product is particularly undesirable when such product is to be reacted with sodium chloroacetate and converted into a surfactant composition with amphoteric properties for the reason that the ester when present tends to reduce the foamability of a product which is undesirable from the standpoint of commercial practicality. So far as is known, prior art processes for making substituted imidazolines do not provide steps to permit one to produce a product imidazoline composition containing less than two weight percent imidazoline.

Consequently, the art needs a new and improved process for making substituted imidazolines in high purity.

BRIEF SUMMARY OF THE INVENTION

The present invention provides a process for making substituted imidazolines which are substantially free from diamide and from byproduct ester as referenced above. While the process of this invention can result in useable products which can contain up to 2 weight percent of such ester, it is naturally preferred and achievable to practice the present invention so as to produce product containing substantially no ester.

In one aspect, the present invention provides a process which results in a reaction with an aminoethyl lower alkanol amine that produces substantially no diamide.

In another aspect, the present invention provides a process for producing substituted imidazolines wherein substantially all of a carboxylic acid ester starting material is convertable into imidazoline with a minimum production of by-products.

In another aspect, the present invention provides a process for producing a substantially pure substituted imidazoline product in high yield from methyl aliphatic monocarboxylate.

In another aspect, the process of the present invention provides a process for producing substituted imidazolines products which contain no more than about 2 weight percent of by-product ester.

In another aspect, the process of the present invention results in product which can contain from about 0.5 weight percent to 3.0 weight percent aminoethyl lower alkanol amine which does not interfere with end use of such product, as in ampholyte production. Surprisingly and unexpectedly the presence of this amine depresses or inhibits formation of unwanted by-product ester impurity.

In another aspect, the present invention provides a process wherein it is surprisingly possible to repair a batch should the batch develop significant quantities of such unwanted ester.

Other and further aspects, aims, objects, advantages, features, and the like for the present invention will be apparent to those skilled in the art from the present specification.

DETAILED DESCRIPTION

In the practice of the process of the present invention, as a first step, one contacts at least one type of methyl ester of an aliphatic monocarboxylic acid containing from 6 through 20 carbon atoms per molecule with an aminoethyl lower alkanol. The contacting is conducted in an inert gaseous atmosphere under anhydrous conditions. The initial mole ratio of methyl carboxylate to aminoethyl lower alkanol amine ranges from about 1:1.1 to 1:2.0. The contacting is conducted while maintaining a temperature ranging from about 160° to 170° C. for a time at least sufficient to substantially completely convert the methyl carboxylate into an aliphatic monoamide by methanol by-product formation between the ester group of the methyl carboxylate and mainly the primary amine group of the amino ethyl lower alkanol amine. The methanol is continuously removed from the reaction zone as a vapor which is preferably condensed in order to avoid atmospheric contamination.

Methyl aliphatic monocarboxylates, i.e. methyl esters as defined above, are well known to the prior art and are items of commerce. In one preferred such starting material, the aliphatic monocarboxylate portion thereof is a residue from lauric acid and so the aliphatic group (not including the carboxyl moiety) contains 11 carbon atoms. In another preferred starting material, the starting methyl ester is derived from coconut oil or similar natural oil source and here the aliphatic groups contain from about 5 to 17 carbon atoms. In another preferred type of methyl carboxylate starting material is a mixture of alkyl radicals derived from the middle portion of coconut oil or similar natural vegetable oil source and so contains from about 11 to 13 carbon atoms per molecule.

Aminoethyl lower alkanol amines are well known to the prior art. By the term "lower" as used herein reference is had to a radical or molecule containing less than 5 carbon atoms each, as the case may be. A preferred aminoethyl lower alkanol amine for the present invention is aminoethyl ethanol amine. Preferably such amino ethyl lower alkanol amine is substantially free from contamination by other amine reactants such as alkylene diamines. For example, it is preferred in the practice of the present invention when using aminoethyl ethanol amine to first subject same to a stripping operation to remove ethylene diamine therefrom. Ethylene diamine should be substantially absent in the starting materials used in the practice of this invention since it can lead to unwanted side reactions and to unwanted contaminants in a substituted imidazoline product.

In general, the starting materials used in the practice of the present invention preferably should each be in a substantially pure form. By the term "substantially pure" reference is had to starting materials containing not more than about 0.05 percent moisture and not more than about 0.02 me/g free acid. Furthermore the aminoethyl alkanolamine preferably should contain not more than about 10 ppm of ethylene diamine.

Suitable inert gases for use in the desired inert gaseous atmosphere used in the contacting can be nitrogen, helium, and the like. Carbon dioxide is undesirable in this process because it is a potential reactant. In addition to serving as a non-oxidizing atmosphere, the inert gas also aids in sweeping out methanol as formed.

The reactions taking place during the contacting step are illustratively theorized using the preferred amine, aminoethyl ethanol amine, to be about as follows:

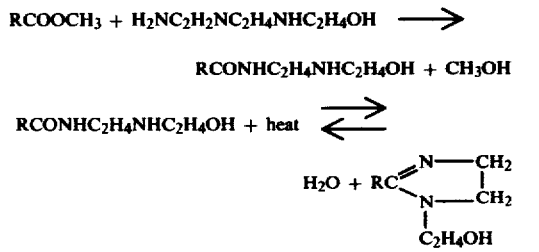

In addition to the illustrated amido amine in equation (3), the following less prominant reaction is theorized to occur:

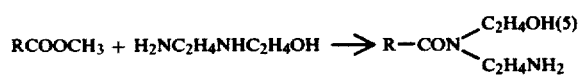

with the suggested amido amine also yielding the desired imidazoline as in equation (4).

Under the conditions described in this invention for this contacting, reaction (3) predominates, while reaction (4) reaches an equilibrium. The product of this contacting step contains about 20 to 25% by weight imidazoline. In order to enhance the inherent selectivity of methyl ester for primary amines, it is the recommended practice of this invention to use a molecular excess of aminoethyl lower alkanolamine, preferably about 1.5 moles of said diamine for every mole of methyl ester as indicated above, the end of this first step is the point in time when all the starting methyl ester has been consumed. This point can be determined by any convenient means. For example, it can be shown by the complete disappearance of an infrared spectral peak at 5.75 microns. Typically this contacting step lasts from about 2 to 6 hours, depending on whether or not catalyst is being used.

Thereafter, one heats, in a step termed herein the first heating step, the resulting reaction product from the contacting step to a temperature ranging from about 195° to 210° C. while maintaining the reactants under a reduced pressure ranging from an initial pressure in the first heating step of about 140 mm Hg to a final pressure of about 60 mm Hg. This first heating step extends for a period of time which is sufficient to substantially completely remove therefrom the theoretical amount of water resulting from a substantially complete conversion of all the aliphatic monoamide into substituted imidazoline so as to obtain one mole imidazoline for every mole of a starting methyl ester added into the reaction zone during the contacting step. This period of time, however, is terminated before, and is insufficient to cause, appreciable production of by-product ester having an infrared peak at 5.75 microns.

This period of time can be determined in any given situation by any convenient means or technique as those skilled in the art will readily appreciate. Sampling of the composition being so first heated is preferred, with analyses being performed on the samples. Infrared spectral examination of samples has been found to be a convenient and preferred analytical procedure for time determination. Thus, in this period of time there progressively occurs a decrease of the amide infrared peak at 6.0 microns and a corresponding increase of the imidazoline infrared peak at 6.25 microns. When, for example, the ratio of the absorbances respectively, of the imidazoline peak to this amide peak reaches a value of not less than about 96 to 4, a presently preferred end point for this firt heating period is indicated. However, those skilled in the art might wish to use another method of end point determination. In practicing the present invention, the total quantity of by-product ester present in a composition at the end of such first heating step should not be in excess of about 2.0 weight percent on a 100 weight percent total such composition basis; preferably such composition is substantially free from ester. Preferably, this first heating step ends with from about 15 to 4 weight percent of amino ethyl lower alkanol amine being present in the resulting composition. Typically, the duration of the first heating step need not exceed about 3 hours although longer and shorter heating times may be used as those skilled in the art will appreciate. During this first heating, the pressure is continuously reduced from an initial pressure to a lower terminal pressure as indicated above. Such a pressure change, it is theorized, operates to continually disrupt the equilibrium existing between dehydration and hydrolysis reaction as shown in equation (4) above, thus speeding this reaction in the desired direction, while at the same time avoiding the premature removal of excess aminoethyl alkanolamine, so as to prevent formation of the unidentified ester by-product.

Thereafter, in a subsequent step, which is herein termed the second heating, the composition obtained in the first heating step is then allowed to cool gradually from an initial temperature of about 200° C. to about 175° C. while maintaining this composition under a pressure continually decreasing from about 60 to about 20 mm Hg. This second heating step is conducted for a time which is sufficient to remove from the reaction zone most, but not all of the unreacted aminoethyl lower alkanolamine without appreciable production of by-product ester. This second heating results in a product composition containing not more than 2 weight percent ester and from about 0.5 to 3.0 weight percent of aminoethyl lower alkanolamine.

In the second heating step, the pressure is continuously reduced from an initial pressure to a lower terminal pressure within the pressure range above indicated. The temperature during this second heating step is continuously reduced from an initial temperature to a lower terminal temperature within the temperature range above indicated.

Typically a product composition produced by the process of this invention on a total 100 percent weight basis comprises:

| | Component | Wt. % Range | Wt. % Preferred |
|---|---|---|---|
| 1. | Substituted imidazoline | at least 94 | at least 97 |
| 2. | By-product ester | 0-2 | nil |
| 3. | Aminoethyl lower alkanol amine | 0.5-3.0 | 1-2 |
| 4. | Alkylamido amine | 0-5 | 0-3 |
| 5. | Catalyst derived soap by-products | 0-1 | 0-0.7 |
| 6. | Diamide | at most 0.05 | nil |

By the term "substantially" as used herein, in relation to "complete" or "free" or the like, reference is had to the circumstance that trace amounts of the material referenced can be present unless otherwise herein specifically defined.

It is a special feature and advantage of the process of the present invention that, when and if formation of said by-product ester occurs at the end of the last step, usually caused by a complete removal of unreacted aminoethyl alkanolamine at high temperature, then one can additionally charge to the reaction mass a quantity of aminoethyl lower alkanol amine. The quantity so charged ranges from about 10 to 40 weight percent (preferably from about 15 to 20 weight percent) of the total 100 weight percent initial quantity of aminoethyl lower alkanol amine present during the initial contacting. Thereafter one reperforms the second heating step in the sequence as described above at least once. Thus, it is a simple matter to repair a batch should ester develop therein by putting in some additional aminoethyl lower alkanol amine and stripping again with care.

Under these conditions, the ester surprisingly disappears.

The practice of the process of the present invention enables one to obtain repeatedly products containing not more than traces of said by-product ester, from about 0.5 to 3% of excess aminoethyl alkanolamine, and not more than 3 weight percent of amide with the balance of a product that is from about 94 to 98 weight percent thereof, being a substantially pure substituted imidazoline which is theorized to have the following structure:

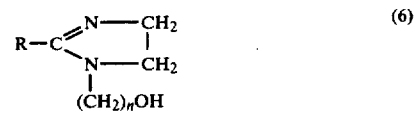

(6)

The amide above indicated is theorized to be a mixture of aliphatic monoamides of which the following is a representative structure:

(7)

in which n = 2−4

Although not necessary, because of its capacity to reduce the contacting time in the initial step of practicing the process of the present invention, it is preferred to conduct the contacting in the presence of at least one transamidification catalyst. Examples of such catalysts include alkali metal lower alkoxides (such as $NaOCH_3$, $KOCH_3$, $KOC(CH_3)_3$ and the like), and organometallic compounds like titanium tetrapropylate. A preferred transamidification catalyst for use in the practice of the present invention is presently sodium methoxide.

The amount of catalyst is selected so that the resulting soap content would not exceed about 1% of the final imidazoline product. The catalyst is added to the reaction zone at the beginning of the contacting step. The usefulness of said catalyst is seen in that the contacting period can be completed in about 1.5-2 hrs., while at least 6 hrs. is necessary to complete the contacting period when no catalyst is being used. The advantage of not using catalyst is in that no sodium soaps are formed so that, if such soaps are undesirable, their formation can easily be avoided without harm to the product.

An outstanding feature of the present invention is that the starting methyl aliphatic monocarboxylate ester enters into reaction with the amino ethyl lower alkanol amine selectively. Thus, such methyl ester during reaction seeks out the primary amine nitrogen functionality with which to combine in preference to the secondary amine functionality in the amino ethyl lower alkanol amine. Such preference for example for the case of methyl stearate is according to K. L. Johnson ("Chemistry, Physics, and Applications of Surface Active Substances", Vol. I, Gordon and Breach Science Publishers, (1967)) said to occur to the extent of 75 mole percent primary and 25 mole % secondary.

The salient feature of fatty acids is an ionic (electrostatic) affinity for amine groups, regardless of whether such amine groups are primary or secondary, an affinity totally absent with methyl esters.

It is therefore, considerably more likely for an amido amine to react with a fatty acid molecule so as to form a diamide, than it is to do so with a methyl ester.

It is a further surprising feature of the present invention that the presence of a small excess amount of amino ethyl lower alkanol amine (i.e. at least 0.5–3% or above) in the first or second heating steps substantially prevents the formation of the by-product ester. At the same time, the presence of such amino ethyl lower alkanol amine has no detrimental effect on any of the properties of the final product substituted imidazoline.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLE 1

214 g. (1.0 mole) of methyl laurate is weighed into a reaction flask and mixed with 156 g (1.5 moles) of aminoethylethanolamine, which has been purified by stripping off a first fraction of about 5 weight percent whereby the content of ethylene diamine was reduced from 250 ppm to about 5 ppm. To this mixture is added 2 g of a 25% solution of $NaOCH_3$ in methanol and the mixture is heated with agitation while bubbling dry nitrogen into the reaction zone. When the temperature reaches about 90° C. methanol starts distilling out of the reaction zone, and the rate of distillation increases as the temperature is brought to 165° C. After one hour at 165° C. a sample is withdrawn and an infrared spectrum of that sample shows that there is still 5.6% methyl ester present. After one additional hour at 165° C. an infrared spectrum and a determination of unreacted aminoethyl ethanol amine (hereinafter designated as AEEA) give the following composition:
  methyl ester: nil
  amide: 60.5%
  imidazoline: 24.3%
  excess AEEA: 15.2% The pressure in the reaction flask is now gradually reduced to 150 mm Hg over a period of about 10 minutes, care being taken to avoid any contact between reactants and air, which would cause rapid and severe darkening of the product, while at the same time the temperature in the reaction zone is raised at 200° C. The reactants are kept at that temperature for a period of two hours while the pressure in the reaction zone is gradually reduced at a rate such that a pressure of 60 mm Hg is reached after the elapse of two hours from the time of reaching the temperature of 200° C. in the reaction zone. At this stage the composition of the reactants is found to be:
ester: nil
amide: 3.3%
imidazoline: 92.1%
AEEA: 4.6% Now the temperature is gradually reduced to 175° C. while the pressure is also reduced gradually to 25 mm Hg over a period of one hour, at the end of which period a complete analysis shows the following composition:
ester: nil
amide: 1.5%
imidazonline: 95.5%
AEEA: 2.2%
Na laurate: 0.75%
free alkali: nil Upon cooling to room temperature without any contact with air the final material is obtained as a straw colored clear liquid which crystallizes after standing overnight to a white solid melting at 43°–46° C. The yield is 274 g.

EXAMPLE 2

The process of Example 1 is repeated except that methyl laurate is replaced with a mixture of methyl esters of a composition corresponding to the molecular distribution of coconut oil, from which the lower fractions of $C_6$, $C_8$, and $C_{10}$ methyl esters have been removed. 231 g of said mixture of methyl esters (1.0 mole) is reacted with 156 g AEEA (1.5 moles) and 2 g of a 25% solution of $NaOCH_3$ in methanol by using the same procedure as described in Example 1. The final material is a straw colored liquid weighing 283 g and having the following composition:
  ester: 0.3%
  amide: 1.2%
  imidazoline: 96.1%
  AEEA: 1.6%
  na cocoate: 0.78% Unlike the material described in Example 1, this liquid does not solidify on standing at room temperature.

EXAMPLE 3

The work described in Example 1 is repeated with the difference that methyl laurate is replaced with a mixture of 70% methyl laurate and 30% methyl myristate. Thus 221 g of mixed ester (1.0 mole) is reacted with 156 g AEEA (1.5 moles) in presence of 2 g of a 25% solution of $NaOCH_3$ in methanol, by using the procedure described in Example 1. At the end of this experiment a straw colored liquid is obtained weighing 280.5 g which only partly crystallizes on standing at room temperature. This liquid has the following composition:
  ester: nil
  amide: 2.2%
  imidazoline: 95.0%
  AEEA: 2.0%
  mixt soap: 0.76%

EXAMPLE 4

The work described in Example 3 is repeated except that no catalyst is added to the reactants. The first stage of this experiment, which consists of holding reactants under a nitrogen blanket at 165° C., has to be extended to about 6 hours in order to completely consume the methyl ester, as attested by periodic infrared measurements. Thereafter, however, the reactant mixture follows the pattern described in Examples 1 through 3. The final material is a straw colored liquid weighing 279 g which has the following composition:
  ester: 0.4%
  amide: 2.3%
  imidazoline: 95.2%
  AEEA: 2.1%
  Na soaps: nil

EXAMPLE 5

The work described in Example 1 is repeated, except for the last step which is conducted at 200° C. without cooling, the pressure is kept at 20 m Hg without gradual adjustments, and the duration of this last step is extended to 3 hours. At the end of this period the composition of the reactant mixture is found to be the following:
  ester: 8.9%
  amide: 2.3%
  imidazoline: 88.1%

AEEA: nil One half of the material is set aside for an experiment described in Example 6, in which it is identified as material 5a. To the remainder of this material is added 15 g AEEA and the second heating step is repeated as described in Example 1, i.e. reactants are heated rapidly to 200° C. under a pressure of 60 mm Hg, then the temperature is allowed to drop to 175° C. while the pressure is gradually reduced to 20 mm over a period of one hour. At the end of this step the reactants have the following composition:

ester: nil
amide: 2.1%
imidazoline: 94.9%
AEEA: 2.3% This material is hereinafter referred to as material 5b.

It is understood that the time periods specified in the above described examples are characteristic only for the particular equipment used for these experiments, and are likely to be different for other types of equipment, depending greatly on physical factors and dimensional variables such as heat transfer, free path, and other conditions dictated by equipment limitations.

EXAMPLE 6

Each material obtained in Examples 1 through 5 is submitted to a reaction with NaOOCH$_2$Cl in an aqueous medium in a manner described in the copending patent application identified as U.S. Ser. No. 901,713, filed on even date herewith, so as to obtain high foaming ampholytes. These ampholytes are then tested for their foaming capability by the well known Ross-Miles method, using 0.1% active solutions in tap water at 25° C. The following results are obtained:

|          | foam height initial | foam height after 5 minutes |
|----------|---------------------|------------------------------|
| material 1 | 19 cm             | 18.5 cm                      |
| 2        | 16 cm               | 16 cm                        |
| 3        | 18 cm               | 17.5 cm                      |
| 4        | 17.5 cm             | 17 cm                        |
| 5a       | 12 cm               | 9 cm                         |
| 5b       | 18 cm               | 17 cm                        |

The mechanism by which the high ester content in material 5a affects the foam of the ampholyte derived from such material is not known, however this effect was found to be consistent for materials containing a high proportion of ester.

We claim:

1. A process for making a substituted imidazoline which is substantially free from diamide and which contains not more than about 2 weight percent on a total product weight basis of byproduct ester, said process comprising the steps of:

(A) contacting in an inert gaseous atmosphere under anhydrous conditions at least one methyl ester of an aliphatic monocarboxylic acid containing from about 6 to about 20 carbon atoms per molecule with aminoethyl lower alkanolamine, the initial mole ratio of said methyl ester to said aminoethyl lower alkanolamine ranging from about 1:1.1 to 1:2.0, while maintaining a temperature ranging from about 160° to 170° C. for a time at least sufficient to substantially completely convert said methyl ester into an aliphatic monoamide by elimination of methanol as a result of reaction between the ester group of said methyl ester and the primary amine group of said aminoethyl lower alkanolamine, (B) thereafter conducting a first heating step under conditions consisting of heating the composition resulting from step (A) to a temperature ranging from about 195° to 210° C. while maintaining the reaction zone under a pressure gradually decreasing from about 140 to about 60 mm Hg over a period of time which is sufficient to substantially completely remove therefrom the theoretical water resulting from a substantially complete conversion of said monoamide into a substituted imidazoline but which time is insufficient to cause appreciable production of byproduct ester, said pressure during this heating period being continuously reduced from an initial pressure to a lower terminal pressure within the pressure range above indicated, and then conducting a (C) second heating step of the resulting composition under conditions consisting of maintaining said resulting composition at a temperature ranging from about 200° to 175° C. under a pressure ranging from about 60 to about 20 mm Hg for a time which results in a product composition containing not more than 2 weight percent of ester and from about 0.5 to 3 weight percent of aminoethyl lower alkanol amine and not less than about 94 weight percent of substituted imidazoline on a 100 weight percent total composition basis said pressure being continuously reduced from an initial pressure to a lower terminal pressure within the pressure range above indicated, said temperature being continuously reduced from an initial temperature to a lower terminal temperature within the temperature range above indicated.

2. The process of claim 1 wherein said contacting is conducted in the presence of at least one transamidification catalyst.

3. The process of claim 2 wherein said catalyst is selected from the group consisting of alkali metal lower alkoxides, and Ti(OPr)$_4$.

4. The process of claim 3 wherein said catalyst is an alkali metal lower alkoxylate.

5. The process of claim 4 wherein said catalyst is sodium methoxylate.

6. The process of claim 1 wherein said aminoethyl lower alkanol amine comprises aminoethyl ethanol amine.

7. The process of claim 1 wherein said aminoethyl lower alkanolamine is substantially free from alkylene diamine.

8. The process of claim 6 wherein said aminoethyl ethanol amine is substantially free from ethylene diamine.

9. The process of claim 1 wherein said initial mole ratio ranges from about 1:1.3 to 1:1.4.

10. The process of claim 1 wherein said temperature ranges from about 162° to 168° C. during said contacting.

11. The process of claim 1 wherein said methyl carboxylate comprises methyl laurate.

12. The process of claim 1 wherein said methyl ester is of an aliphatic carboxylic acid mixture containing from about 12 to 16 carbon atoms per molecule and wherein the carboxylate radicals are derived from a vegetable oil.

13. The process of claim 1 wherein said methyl ester comprises a mixture of methyl esters of aliphatic carboxylic acids containing from about 10 to 18 carbon atoms per molecule.

14. The method of claim 1 wherein, during said first heating step, said resulting composition is heated at a temperature ranging from about 198° to 205° C. under a pressure ranging from about 110 to 80 mm Hg.

15. The method of claim 1 wherein during said second heating step, said resulting composition is maintained at a temperature ranging from about 195° to 180° C. under a pressure ranging from about 50 to 30 mm Hg.

16. The method of claim 1 wherein the product of said heating step (B) comprises at least one imidazoline characterized by the structure:

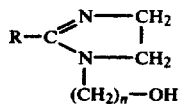

wherein
R is an aliphatic radical containing from about 5 to 19 carbon atoms per molecule, and
n is a positive whole number of from 2 through 4.

17. In a process for making a substituted imidazoline which is substantially free from diamide and which contains not more than about 2 weight percent on a total product weight basis of byproduct ester, said process comprising the steps of:

(A) contacting in an inert gaseous atmosphere under anhydrous conditions at least one methyl ester of an aliphatic monocarboxylic acid containing from about 6 to about 20 carbon atoms per molecule with aminoethyl lower alkanolamine, the initial mole ratio of said methyl ester to said aminoethyl lower alkanoalamine ranging from about 1:1.1 to 1:2.0, while maintaining a temperature ranging from about 160° to 170° C. for a time at least sufficient to substantially completely convert said methyl ester into an aliphatic monamide by elimination of methanol as a result of reaction between the ester group of said methyl ester and the primary amine group of said aminoethyl lower alkanolamine, (B) thereafter conducting a first heating step under conditions consisting of heating the composition resulting from step (A) to a temperature ranging from about 195° to 210° C. while maintaining the reaction zone under a pressure gradually decreasing from about 140 to about 60 mm Hg over a period of time which is sufficient to substantially completely remove therefrom the theoretical water resulting from a substantially complete conversion of said monoamide into a substituted imidazoline but which time is insufficient to cause appreciable production of byproduct ester, said pressure during this heating period being continuously reduced from an initial pressure to a lower terminal pressure within the pressure range above indicated, and then conducting a (C) second heating step of the resulting composition under conditions consisting of maintaining said resulting composition at a temperature ranging from about 200° to 175° C. under a pressure ranging from about 60 to about 20 mm Hg for a time which results in a product composition containing not more than 2 weight percent of ester and from about 0.5 to 3 weight percent of aminoethyl lower alkanol amine and not less than about 94 weight percent of substituted imidazoline on a 100 weight percent total composition basis said pressure being continuously reduced from an initial temperature to a lower terminal temperature within the temperature range above indicated, the improvement which comprises th step of when and if formation of such byproduct ester occurs, as shown by the pressure of an infrared peak at 5.75 microns either at the end of step (B), or at the end of step (C), additionally charging a quantity of aminethyl lower alkanol amine to such reaction composition which quantity ranges from about 10 to 40 weight percent of the initial quantity of amino ethyl lower alkanol amine present in said contacting, and thereafter performing said step (C) in sequence as defined at least once.

* * * * *